United States Patent
Han et al.

(10) Patent No.: US 10,406,005 B2
(45) Date of Patent: Sep. 10, 2019

(54) STENT AND METHOD FOR MANUFACTURING SAME

(71) Applicant: M.I.TECH CO., LTD., Pyeongtaek-si, Gyeonggi-do (KR)

(72) Inventors: Jong Hyeon Han, Seoul (KR); Hun Kuk Park, Pyeongtaek-si (KR); Bong Seok Jang, Osan-si (KR); Ho Yun, Asan-si (KR)

(73) Assignee: M.I. TECH CO., LTD., Pyeongtaek-si (KR)

( * ) Notice: Subject to any disclaimer, the term of this patent is extended or adjusted under 35 U.S.C. 154(b) by 331 days.

(21) Appl. No.: 15/307,263

(22) PCT Filed: May 13, 2015

(86) PCT No.: PCT/KR2015/004782
§ 371 (c)(1),
(2) Date: Oct. 27, 2016

(87) PCT Pub. No.: WO2015/174730
PCT Pub. Date: Nov. 19, 2015

(65) Prior Publication Data
US 2017/0049589 A1 Feb. 23, 2017

(30) Foreign Application Priority Data
May 13, 2014 (KR) .................... 10-2014-0057008

(51) Int. Cl.
*A61F 2/86* (2013.01)
*A61F 2/07* (2013.01)
(Continued)

(52) U.S. Cl.
CPC .................. *A61F 2/86* (2013.01); *A61F 2/07* (2013.01); *A61F 2/90* (2013.01); *A61L 27/34* (2013.01);
(Continued)

(58) Field of Classification Search
CPC ...... A61F 2/07; A61F 2/86; A61F 2/89; A61F 2/90; A61F 2002/072; A61F 2210/0076;
(Continued)

(56) References Cited

U.S. PATENT DOCUMENTS 5,662,713 A * 9/1997 Andersen .................. A61F 2/90
128/898
5,693,085 A * 12/1997 Buirge .................. A61F 2/0022
606/192
(Continued)

FOREIGN PATENT DOCUMENTS

CN 1358482 A 7/2002
CN 101496753 A 8/2009
(Continued)

OTHER PUBLICATIONS

International Search Report dated Aug. 17, 2015, issued to International Application No. PCT/KR2015/004782.
(Continued)

Primary Examiner — Ryan J. Severson
(74) Attorney, Agent, or Firm — Stein IP, LLC

(57) ABSTRACT

The present invention relates to a stent and a method for manufacturing the same. The stent includes: a first hollow cylindrical body portion formed by weaving a metal wire; a second hollow cylindrical body portion formed by weaving a metal wire, and configured to surround the first body portion; an integral portion configured to form two adjacent ends of the first body portion and the second body portion integrally; and a membrane inserted between the first body portion and the second body portion, and configured to surround the outside of the first body portion. According to the present invention, there is no risk of the film being torn when the stent is bent, an additional connection wire is not required, the process of manufacturing the stent is simple,
(Continued)

and the costs required for the manufacture of the stent are not high.

5 Claims, 10 Drawing Sheets

(51) Int. Cl.
    *A61L 27/34*     (2006.01)
    *A61F 2/90*     (2013.01)
    *A61L 31/02*     (2006.01)
    *A61L 31/10*     (2006.01)
    *A61L 31/14*     (2006.01)

(52) U.S. Cl.
    CPC ............. *A61L 31/022* (2013.01); *A61L 31/10* (2013.01); *A61L 31/14* (2013.01); *A61F 2230/0069* (2013.01); *A61F 2240/001* (2013.01); *A61L 2420/02* (2013.01)

(58) Field of Classification Search
    CPC ...... A61F 2220/0025; A61F 2230/0069; A61F 2250/0039
    See application file for complete search history.

(56) References Cited

U.S. PATENT DOCUMENTS

| | | | | |
|---|---|---|---|---|
| 5,876,445 A * | 3/1999 | Andersen | ........... | A61F 2/04 623/23.7 |
| 6,146,416 A * | 11/2000 | Andersen | ........... | A61F 2/90 623/1.15 |
| 6,156,064 A * | 12/2000 | Chouinard | ........... | A61F 2/07 623/1.44 |
| 6,245,100 B1 | 6/2001 | Davila et al. | ........... | 623/1.13 |
| 6,305,436 B1 * | 10/2001 | Andersen | ........... | A61F 2/04 140/107 |
| 6,355,070 B1 * | 3/2002 | Andersen | ........... | A61F 2/90 606/198 |
| 6,391,052 B2 * | 5/2002 | Buirge | ........... | A61F 2/0022 204/499 |
| 6,505,654 B1 * | 1/2003 | Andersen | ........... | A61F 2/90 140/107 |
| 6,669,724 B2 * | 12/2003 | Park | ........... | A61F 2/2418 623/1.24 |
| 6,709,455 B1 * | 3/2004 | Chouinard | ........... | A61F 2/07 623/1.13 |
| 6,911,040 B2 * | 6/2005 | Johnson | ........... | A61F 2/07 623/1.13 |
| 7,182,788 B2 * | 2/2007 | Jung | ........... | A61F 2/07 623/23.68 |
| 7,497,872 B2 * | 3/2009 | Melsheimer | ........... | A61F 2/07 623/1.13 |
| 8,043,355 B2 | 10/2011 | Shin et al. | ........... | 623/1.13 |
| 9,439,790 B2 * | 9/2016 | Clerc | ........... | A61F 2/07 |
| 9,535,590 B2 | 1/2017 | Danton et al. | ........... | 715/205 |
| 2001/0034550 A1 * | 10/2001 | Buirge | ........... | A61F 2/0022 623/1.47 |
| 2002/0183828 A1 * | 12/2002 | Park | ........... | A61F 2/2418 623/1.15 |
| 2003/0139797 A1 | 7/2003 | Johnson et al. | ........... | 623/1.13 |
| 2004/0044402 A1 * | 3/2004 | Jung | ........... | A61F 2/07 623/1.24 |
| 2004/0167606 A1 * | 8/2004 | Chouinard | ........... | A61F 2/07 623/1.13 |
| 2007/0135906 A1 * | 6/2007 | Badylak | ........... | A61F 2/0022 623/1.44 |
| 2009/0187240 A1 | 7/2009 | Clerc et al. | ........... | 623/1.17 |
| 2010/0049302 A1 | 2/2010 | Kang et al. | ........... | 623/1.15 |
| 2017/0014133 A1 * | 1/2017 | Han | ........... | A61F 2/90 |
| 2017/0049589 A1 * | 2/2017 | Han | ........... | A61L 27/34 |
| 2018/0263626 A1 * | 9/2018 | Han | ........... | A61F 2/90 |

FOREIGN PATENT DOCUMENTS

| | | |
|---|---|---|
| JP | 2001-327609 A | 11/2001 |
| JP | 2010-521217 A | 6/2010 |
| JP | 2011-509758 A | 3/2011 |
| KR | 10-0847432 B1 | 7/2008 |
| KR | 10-0988816 B1 | 10/2010 |
| KR | 10-2012-0073496 A | 7/2012 |
| KR | 10-2012-0098188 A | 9/2012 |
| WO | WO 2011/043500 A1 | 4/2011 |

OTHER PUBLICATIONS

Japanese Office Action dated Aug. 25, 2017, issued by the Japanese Patent Office in corresponding application JP 201580026217.2.

Japanese Office Action dated Sep. 22, 2017, issued by the Japanese Patent Office in corresponding application JP 2016-564339.

Korean Office Action dated Oct. 23, 2015, issued by the Korean Intellectual Property Office in corresponding application KR 10-2014-0057008.

* cited by examiner

STENT AND METHOD FOR MANUFACTURING SAME

CROSS-REFERENCE TO RELATED APPLICATIONS

This application is a national stage of International Application No. PCT/KR2015/004782, filed May 13, 2015, which claims the benefit of priority to Korean Application No. 10-2014-0057008, filed May 13, 2014, in the Korean Intellectual Property Office, the disclosures of which are incorporated herein in their entireties by reference.

TECHNICAL FIELD

The present invention relates to a stent and a method for manufacturing the same.

BACKGROUND ART

Generally, stents are cylindrical medical devices that are implanted to widen or open stenosed portions when lumens inside human bodies are stenosed by diseases developed inside the human bodies and, thus, the functions of the lumens are degraded or the lumens cannot perform any functions.

As a representative, a self-expandable stent is being most widely used. By using the shape memory effect of shape memory alloy, the stent having a cylindrical mesh shape acts to be implanted into a lumen in the state of being contracted to have a small diameter and to then restore its original diameter by means of the shape memory effect and expand a stenosed portion.

Only if the self-expandable stent has expandability for expansion of a lumen, flexibility for flexible adaptation to a bent portion of a lumen while maintaining the bent shape of the lumen without a change, and reducibility for reduction to a predetermined diameter, the stent can appropriately perform its functionality.

A conventional stent constitutes a double stent, in which an inner stent and an outer stent are superimposed on each other and a film-shaped coating is formed, in order to prevent a phenomenon in which the stent is moved from an initial installation location and prevent tissues from growing and invading into a mesh constituting a part of the stent due to the growth of the tissues, thereby preventing stenosis from occurring again. However, the above-described double stent requires an additional connection wire that couples the inner stent and the outer stent to each other. A film is formed through a coating process, and thus the film may be torn when the stent is bent in accordance with the shape of the bent lumen. Accordingly, the conventional stent is problematic in that a manufacturing process is complicated and manufacturing costs are high.

A conventional technology related to the above technology includes "Triple Structure Stent" disclosed in Korean Patent Application Publication No. 10-2012-0098188.

DISCLOSURE

Technical Problem

The present invention provides a stent and a method for manufacturing the same, in which an additional connection wire is not required, a manufacturing process is simple, manufacturing costs are not high, and a film is not easily torn when the stent is bent.

Technical Solution

According to the present invention, there is provided a stent, including: a first hollow cylindrical body portion formed by weaving a metal wire; a second hollow cylindrical body portion formed by weaving a metal wire, and configured to surround the first body portion; an integral portion configured to integrally combine two adjacent ends of the first body portion and the second body portion; and a membrane inserted between the first body portion and the second body portion, and configured to surround the outside of the first body portion.

Furthermore, the stent according to the present invention may further include a coating film applied onto the integral portion.

Furthermore, the membrane and the coating film partially overlap each other. the membrane and the coating film may be made of one selected from the group consisting of polytetrafluoroethylene (PTFE), silicone, polyurethane, polyester, polypropylene, polyethylene, polyolefin, high density polyethylene (HDPE), and expanded polytetrafluoroethylene (ePTFE).

According to the present invention, there is provided a method for manufacturing a stent, the method including: a first step of performing heat treatment on a stent, including a first hollow cylindrical body portion formed by weaving a wire made of shape memory alloy, a second body portion configured to surround the first body portion, and an integral portion configured to integrally combine two adjacent ends of the first body portion and the second body portion; a second step of forming an opening by unweaving the wire of an ending portion, close to the integral portion at one end of the second body portion, in a circumferential direction and thus separating the second body portion into two portions; a third step of fastening an end of the integral portion, close to the ending portion, to a drawing guide; a fourth step of inserting the integral portion, close to the ending portion, and the first body portion into a tube having a diameter smaller than that of the first body portion by drawing the drawing guide through the tube, and forming an insertion space between the tube and the second body portion by inserting the tube between the first body portion and the second body portion through the opening; a fifth step of inserting a membrane into the insertion space through the tube, and inserting the membrane between the first body portion and the second body portion by removing the tube; and a sixth step of combining the separate portions of the second body portion integrally by reweaving the unwoven wire.

Furthermore, the method according to the present invention may further include, after the sixth step, a seventh step of forming a coating film by coating the integral portion with coating material.

Advantageous Effects

The present invention provides the stent and the method for manufacturing the stent that are configured such that the first body portion and the second body portion are integrally formed by the integral portion formed at two adjacent ends thereof and a Teflon film with folds is inserted between the first body portion and the second body portion, so that an additional connection wire is not required, there is no risk of the Teflon film being torn when the stent is bent, the process of manufacturing the stent is simple, and the costs required for the manufacture of the stent are not high.

MODE FOR INVENTION

A stent 100 of the present invention will be described in greater detail below via embodiments and the accompanying views.

Figure 1:
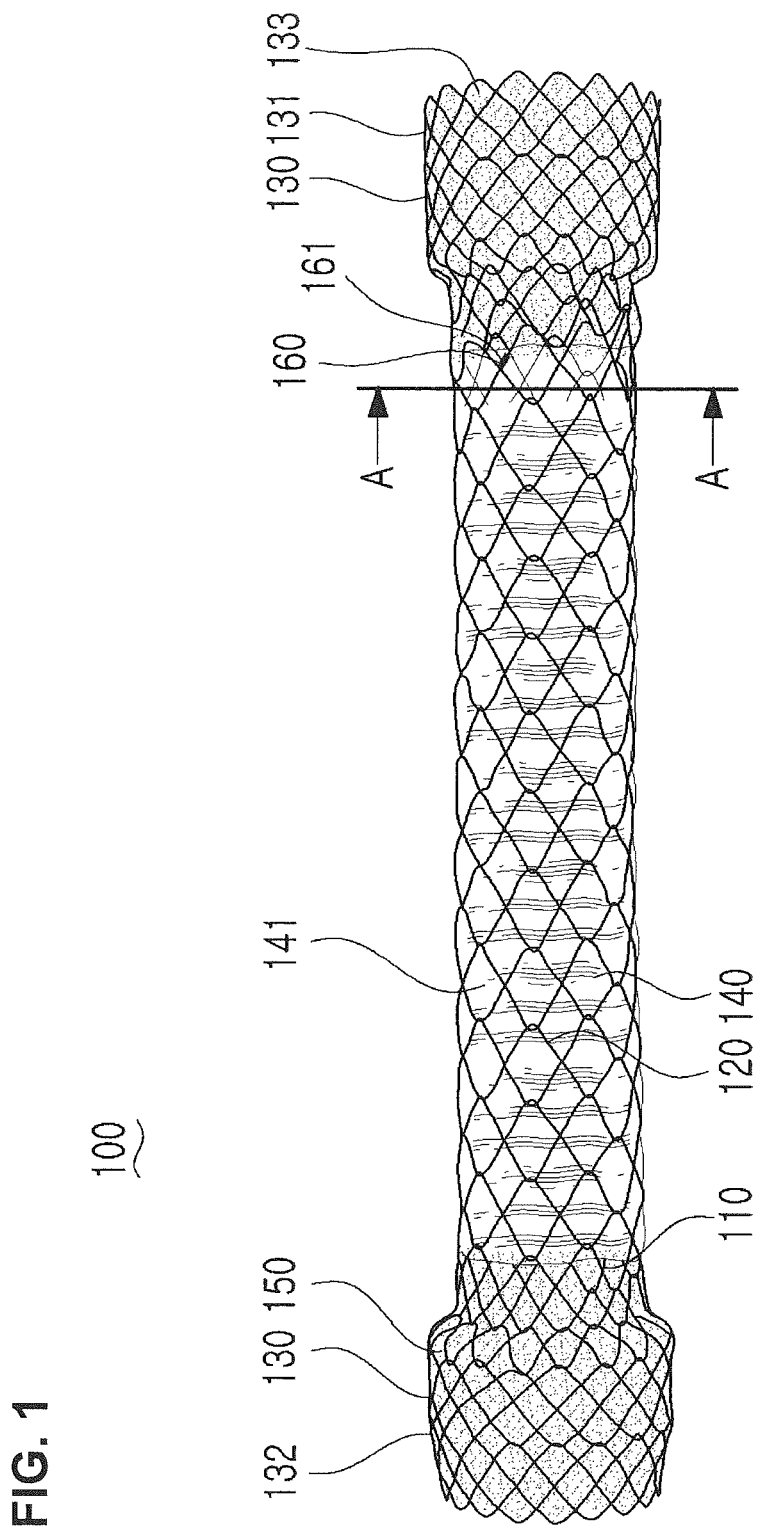
FIG. 1 is a front perspective view showing a stent according to an embodiment of the present invention.

FIG. 1 is a front perspective view showing a stent 100 according to an embodiment of the present invention.

Referring to FIG. 1, the stent 100 according to the embodiment of the present invention includes a first body portion 110, a second body portion 120, integral portions 130, a membrane 140, and a coating film 150.

As shown in FIG. 1, the first body portion 110 and the second body portion 120 are formed by weaving a metal wire or metal wires, and have a hollow cylindrical shape. The second body portion 120 surrounds the first body portion 110, and can be freely moved because the second body portion 120 is spaced from the first body portion 110. Accordingly, when the stent is implanted into a stenosed portion of a bent lumen, it can be deformed in accordance with the shape of the stenosed portion, and thus stimuli to the lumen are reduced. Furthermore, an ending portion 160 in which the weaving of the metal wire ends is formed in a portion of one end of the second body portion 120 close to one of the integral portions 130, and the ending portion 160 prevents the woven metal wire from being unwoven by means of an ending band 161. The first body portion 110 forms a basic skeleton that expands a stenosed portion of a lumen. The second body portion 120 prevents the stent from moving in such a manner that, after the stent has been implanted into a stenosed portion, tissues enter into the stent and the tissues and the structure of the stent are overlapped. Although the metal wire(s) may be made of shape memory alloy and the shape memory alloy may be nitinol, the metal wires and the shape memory alloy are not limited thereto. The thickness of the metal wire constituting the first body portion 110 may be identical with or different from that of the metal wire constituting the second body portion 120.

The integral portions 130 include a first integral portion 131 and a second integral portion 132, and have a hollow cylindrical shape. Each of the integral portions 130 combines two adjacent ends of the first body portion 110 and the second body portion 120 together. One end of the first body portion 110 and one end of the second body portion 120 are combined together by the first integral portion 131, and the other end of the first body portion 110 and the other end of the second body portion 120 are combined together by the second integral portion 132. The diameter of the integral portions 130 are formed to be larger than that of the second body portion 120. The integral portions 130 facilitate the implantation of the first body portion 110 and the second body portion 120 into a stenosed portion, and prevent the stent implanted into the stenosed portion from moving.

The membrane 140 has a cylindrical shape, and is inserted between the first body portion 110 and the second body portion 120. The membrane 140 surrounds the first body portion 110, and is provided with folds 141 horizontally so that the membrane 140 can be extended or shortened in the lengthwise direction of the first body portion 110. The membrane 140 according to an embodiment of the present invention may be made of expanded polytetrafluoroethylene (ePTFE). Since ePTFE is flexible, stimuli to a bent lumen is reduced when the stent is implanted into a stenosed portion of the bent lumen.

The coating film 150 is applied onto the integral portions 130, and are formed by spraying and immersing the integral portions 130 with and in liquid coating material and hardening the liquid coating material through heat treatment. The coating film 150 according to an embodiment of the present invention may be made of silicone. Since the silicone has desirable flexibility, it facilitates loading into insertion equipment. Furthermore, since the silicone is stiffened by being hardened after being applied onto the integral portions 130, it has stronger force that acts to extend a stenosed portion of a lumen. Accordingly, when the stent is implanted into a stenosed portion, the integral portions 130 coated with the silicone strongly extend the stenosed portion, and thus the first body portion 110 and the second body portion 120 can be easily implanted into the stenosed portion.

Figure 2:
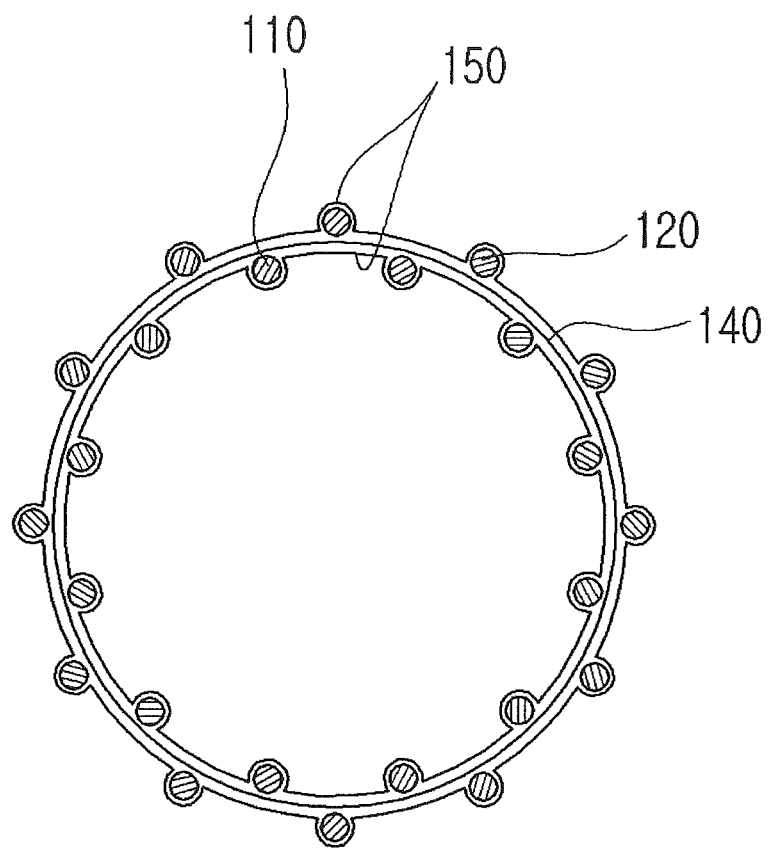
FIG. 2 is a sectional view of the stent taken along line A-A of FIG. 1.

FIG. 2 is a sectional view of the stent taken along line A-A of FIG. 1. Referring to FIG. 2, the coating film 150 according to an embodiment of the present invention may overlap the membrane 140. Accordingly, this can reliably prevent tissues from intruding into the first body portion 110 and the integral portion 130 due to the growth of the tissues, thereby preventing stenosis from occurring again.

Although the membrane 140 and the coating film 150 may be made of one selected from the group consisting of polytetrafluoroethylene (PTFE), silicone, polyurethane, polyester, polypropylene, polyethylene, polyolefin, high density polyethylene (HDPE), and expanded polytetrafluoroethylene (ePTFE), they are not limited thereto.

Figure 3:
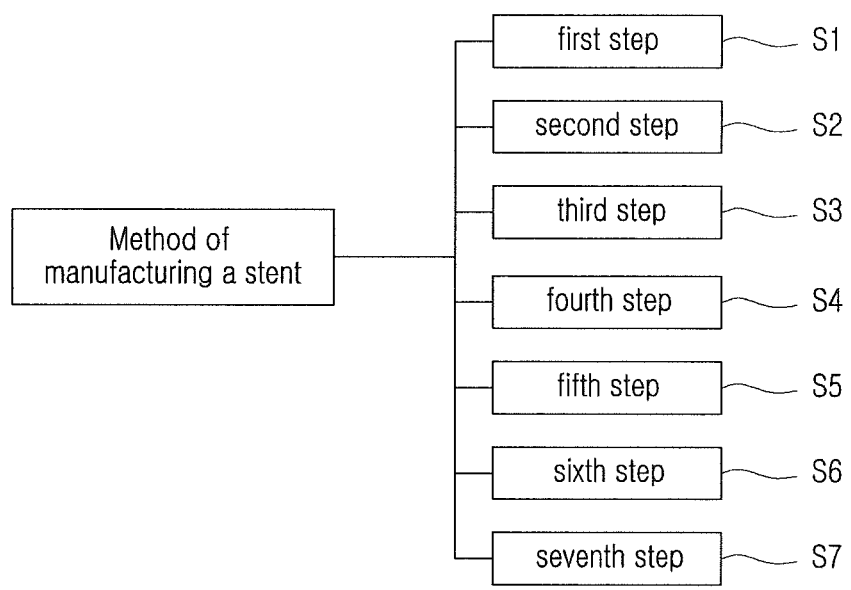
FIG. 3 is a diagram showing a method for manufacturing a stent according to an embodiment of the present invention.

FIG. 3 is a diagram showing a method for manufacturing a stent according to an embodiment of the present invention, and FIGS. 4 to 10 are views sequentially showing the method for manufacturing a stent according to the embodiment of the present invention.

Referring to FIG. 3, the method for manufacturing a stent according to the embodiment of the present invention includes: a first step S1 of performing heat treatment on a stent; a second step S2 of forming an opening by separating a second body portion 120; a third step S3 of fastening an end of an integral portion 130 close to an ending portion 160 to a drawing guide 170; a fourth step S4 of passing the drawing guide 170 through a tube, and inserting the integral portion 130, close to the ending portion 160, and a first body portion 110 into the tube; a fifth step S5 of inserting a membrane 140 between the tube and the second body portion 120, and removing the tube; a sixth step S6 of combining the separate portions of the second body portion 120 together, and a seventh step S7 of forming a coating film 150 on the integral portion 130.

At the first step S1, the shape of the stent is maintained by performing heat treatment on the stent in which the first body portion 110 and the second body portion 120 are integrally formed by integral portions 130. The first body portion 110 and the second body portion 120, surrounding the first body portion 110, are hollow cylindrical portions that are formed by weaving wires made of shape memory alloy. Accordingly, the shape memory alloy forming the stent remembers the original shape of the stent through heat treatment.

Figure 4:
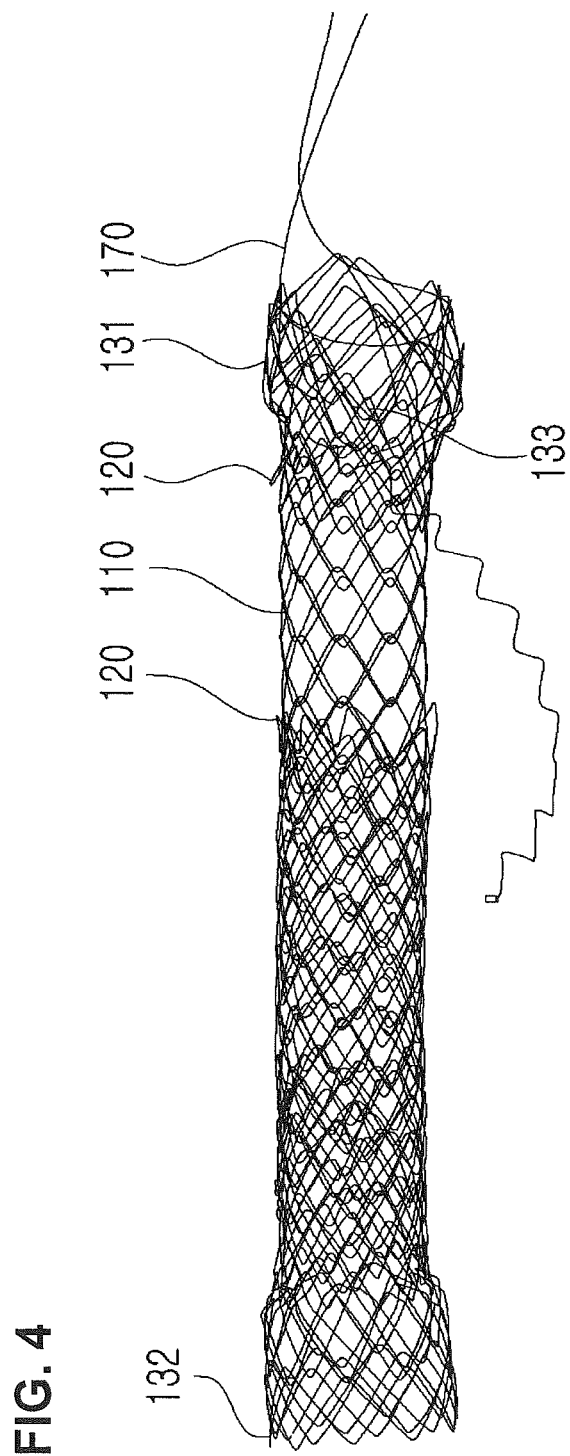
FIGS. 4 to 10 are views sequentially showing the method for manufacturing a stent according to the embodiment of the present invention.

Referring to FIG. 4, at the second step S2, an opening is formed by fully unweaving the wire of the ending portion 160 close to the integral portion 130 at one end of the second body portion 120 in a circumferential direction and thus separating the second body portion 120 into two portions. Accordingly, a path along which a membrane 140 can be inserted is formed between the first body portion 110 and the second body portion 120. The membrane 140 may be an expanded polytetrafluoroethylene (ePTFE) film. The ending portion 160 is formed in the second body portion 120, and ends with an ending band 161 when the weaving of the stent ends. The ending band 161 is disposed at a location close to any one of the first integral portion 131 and the second integral portion 132. The ending band 161 according to an embodiment of the present invention is disposed at a location close to the first integral portion 131. The ending band 161 is easy to mount and remove.

At the third step S3, an end of the first integral portion 131 close to the ending portion 160 is fastened to the drawing guide 170. Although the drawing guide 170 may be a thread or a wire that can guide the end of the first integral portion 131 and the first body portion 110 into the tube, it is not limited thereto. According to an embodiment of the present invention, the drawing guide 170 is passed through a diamond-shaped space portion 133 formed at the end of the integral portion in a circumferential direction in a zigzag manner, and fastens the integral portion 131. When the drawing guide 170 is drawn, the integral portion 131 closes up. Accordingly, the drawing guide 170 can guide the integral portion 131 and the first body portion 110 into the tube 180 having a diameter smaller than that of the first body portion 110.

Figure 5:
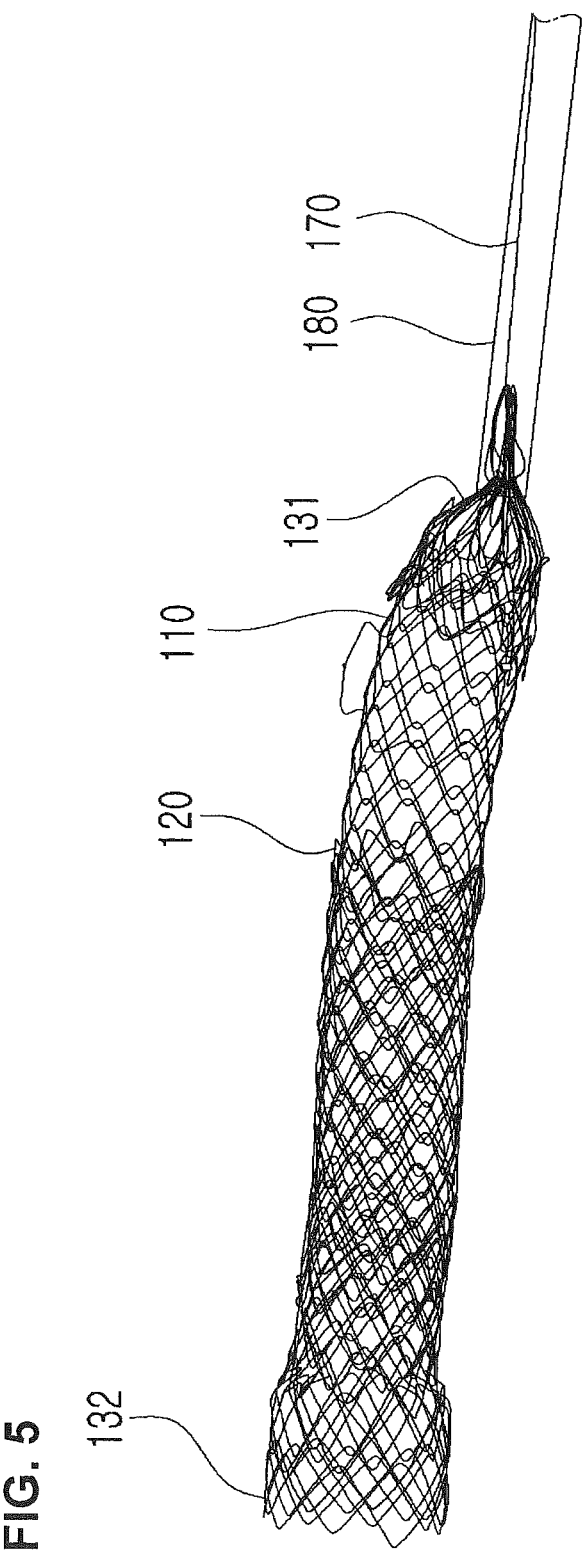
Figure 6:
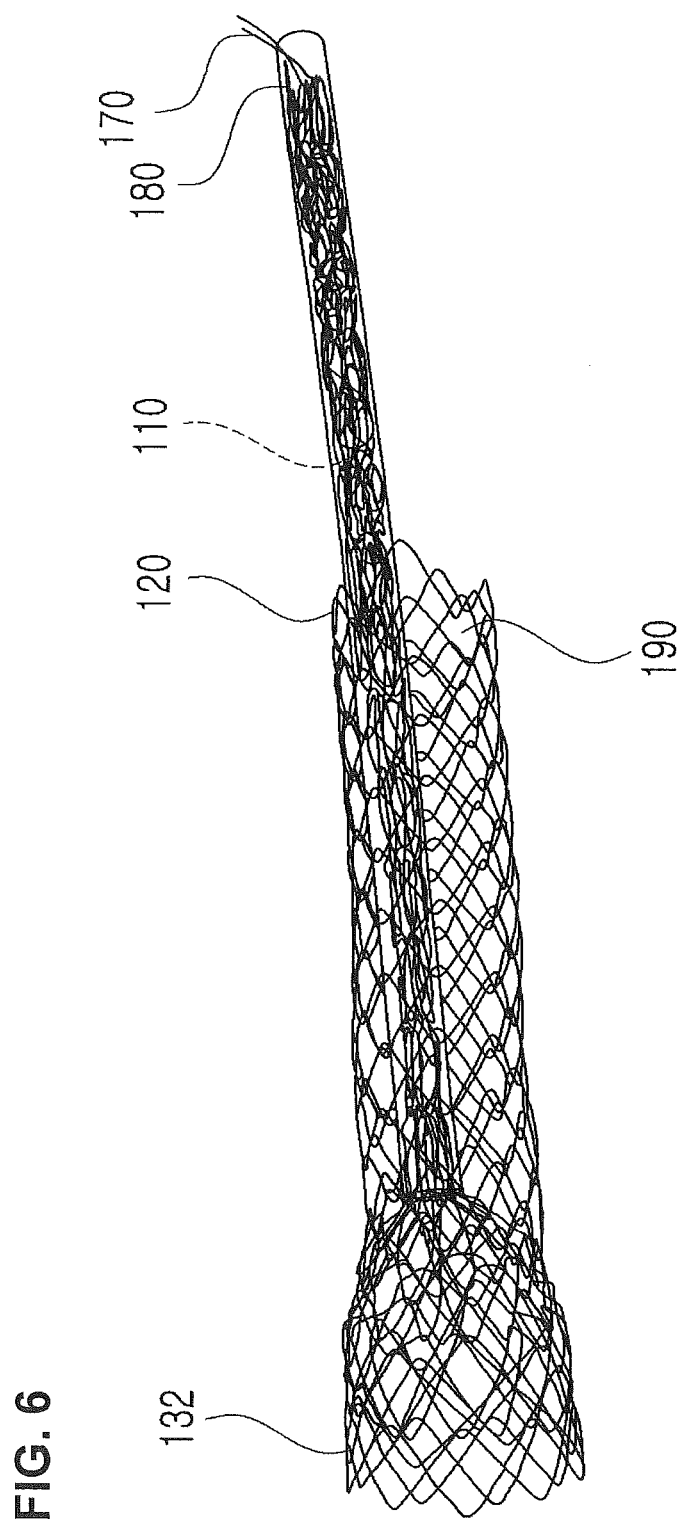

Referring to FIGS. 5 and 6, at the fourth step S4, when the drawing guide 170 is drawn through the tube 180 having a diameter smaller than that of the first body portion 110, the first integral portion 131, close to the ending portion, and the first body portion 110 are inserted into the tube 180, the tube 180 is inserted between the first body portion 110 and the second body portion 120 through the opening, and an insertion space 190 is formed between the tube 180 and the second body portion 120.

Figure 7:
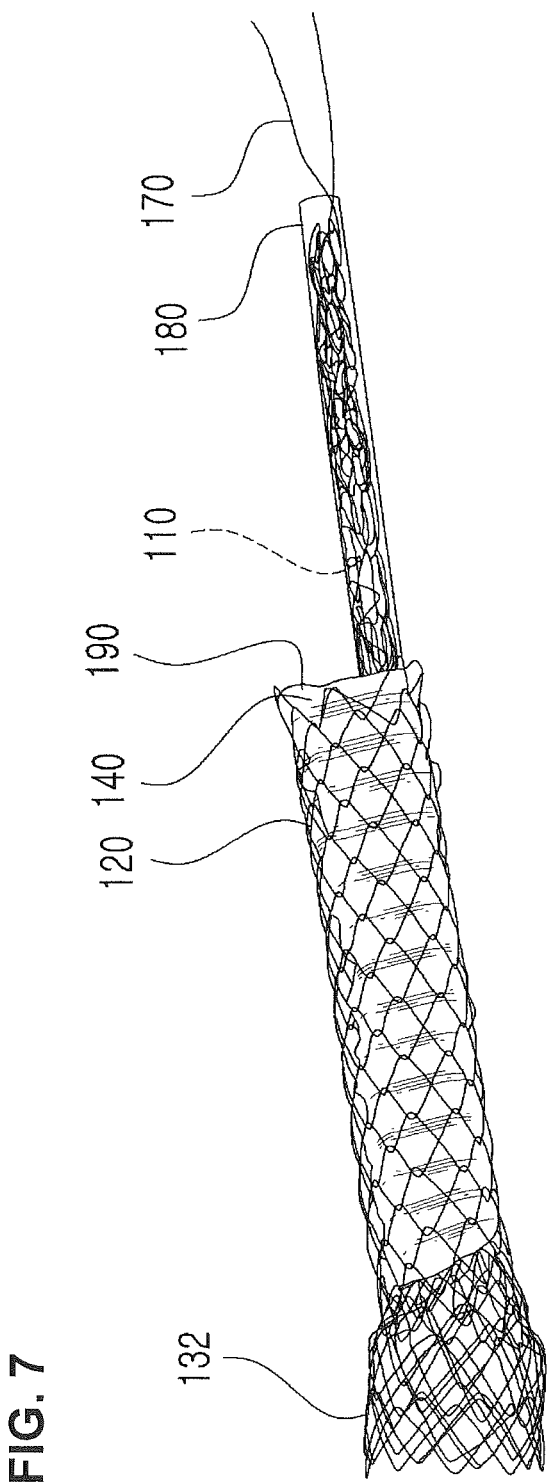
Figure 8:
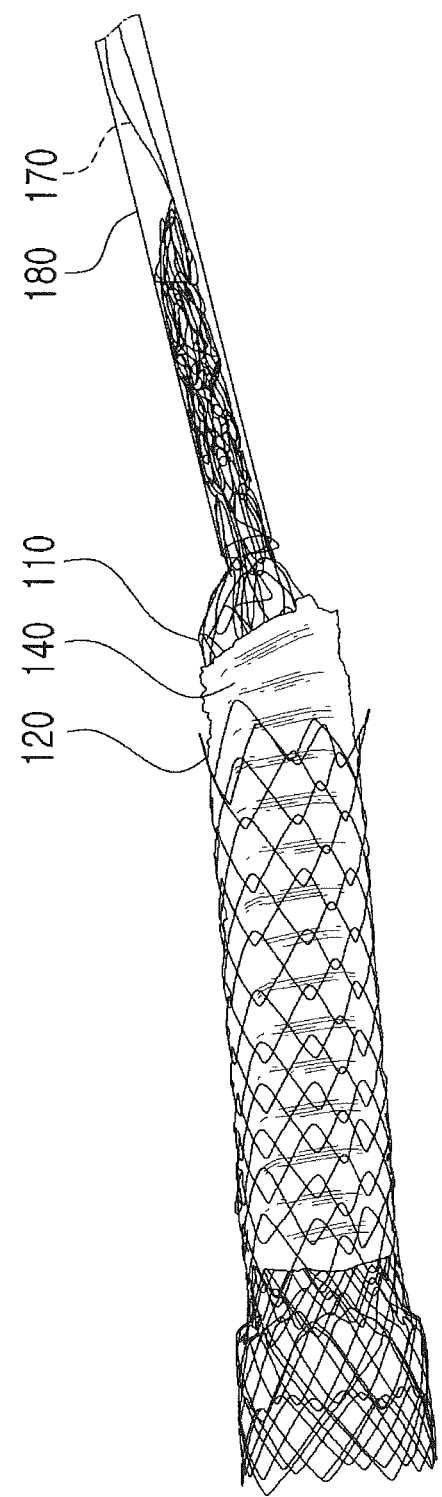

Referring to FIGS. 7 and 8, at the fifth step S5, a membrane 140 is inserted into the insertion space 190 via the tube 180. When the tube 180 is removed after the membrane 140 has been inserted, the first body portion 110 is restored to its original shape, and the membrane 140 is disposed between the first body portion 110 and the second body portion 120.

Figure 9:
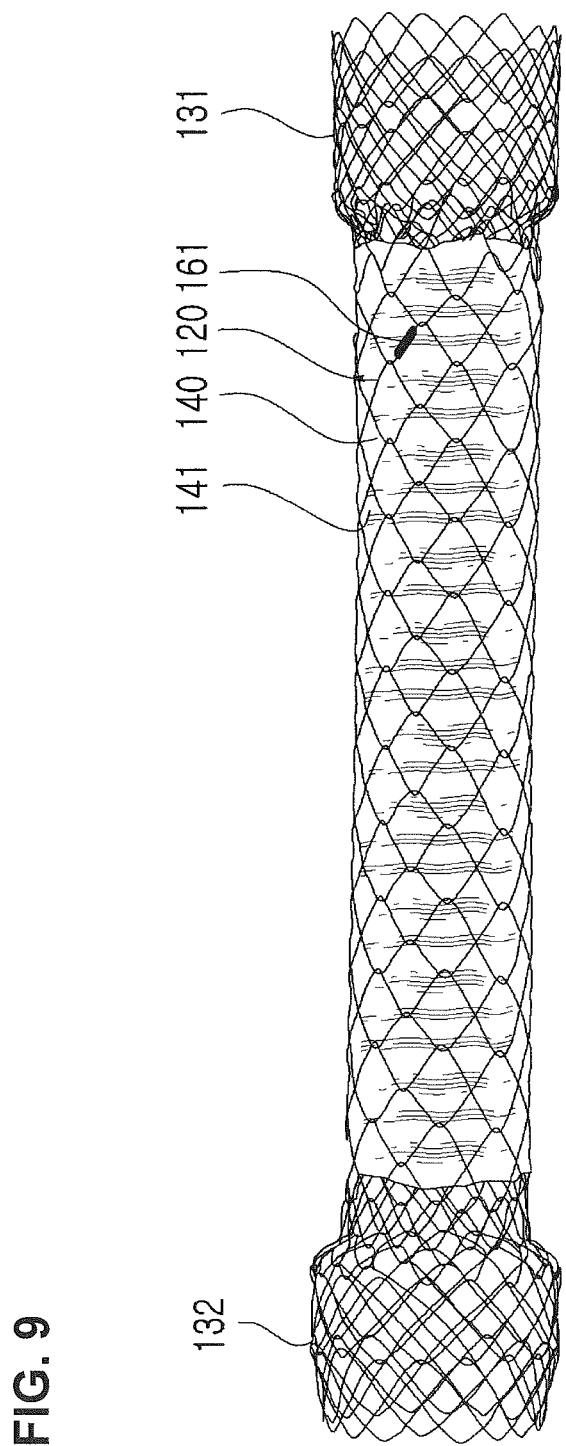

Referring to FIG. 9, at the sixth step S6, the unwoven wire is rewoven in a circumferential direction and integrally forms the second body portion 120. Ending is performed using an ending band 161. The ending band 161 is integrally combined with the wire of the stent. Thus, when the stent is implanted into a lumen, inconvenient stimuli are not provided to the lumen.

Figure 10:
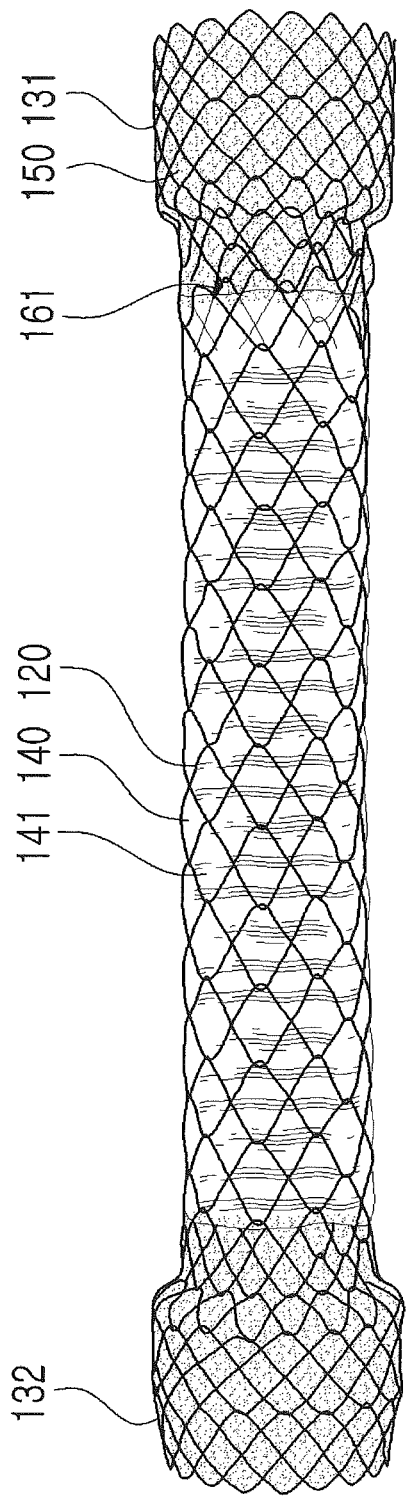

Referring to FIG. 10, at the seventh step S7, a coating film 150 is formed by coating the integral portion 130 with coating material. Although the coating film 150 may be a silicone film, it is not limited thereto. According to an embodiment of the present invention, the coating film 150 may be formed to overlap the membrane 140. Accordingly, the present invention can reliably prevent tissues from growing and intruding into the stent, thereby preventing stenosis from occurring again. The coating film 150 is formed by spraying and immersing the integral portion with and in liquid coating material and hardening the liquid coating material through heat treatment.

The membrane 140 and the coating film 150 may be made of one selected from the group consisting of polytetrafluoroethylene (PTFE), silicone, polyurethane, polyester, polypropylene, polyethylene, polyolefin, high density polyethylene (HDPE), and expanded polytetrafluoroethylene (ePTFE).

It will be apparent to those having ordinary knowledge in the art to which the present invention pertains that the present invention is not limited to the embodiments but may be modified or altered in various manners and practiced Within a range that does not depart from the technical gist of the present invention.

DESCRIPTION OF REFERENCE SYMBOLS

| | |
|---|---|
| 100: stent | 140: film |
| 110: first body portion | 141: fold |
| 120: second body portion | 150: coating |
| 130: expanded portion | 160: ending portion |
| 131: first expanded portion | 161: ending band |
| 132: second expanded portion | 170: drawing guide |
| 133: space portion | 180: tube |
| 190: insertion space | |

The invention claimed is:

1. A stent, comprising:
a first hollow cylindrical body portion formed by weaving a metal wire;
a second hollow cylindrical body portion formed by weaving a metal wire, and configured to surround the first body portion;
an integral portion configured to combine two adjacent ends of the first body portion and the second body portion integrally, a diameter of the integral portion being configured to be larger than a diameter of the second body portion; and
a membrane inserted between the first body portion and the second body portion, and configured to surround an outside of the first body portion.

2. The stent of claim 1, further comprising a coating film applied onto the integral portion.

3. The stent of claim 2, wherein the membrane and the coating film partially overlap each other.

4. The stent of claim 2, wherein the membrane and the coating film are made of one selected from the group consisting of PTFE, silicone, polyurethane, polyester, polypropylene, polyethylene, polyolefin, HDPE, and ePTFE.

5. The stent of claim 1, wherein the integral portion includes a first integral portion and a second integral portion, the first integral portion being configured to combine one end of the first body portion and one end of the second body portion, the second integral portion being configured to combine the other end of the first body portion and the other end of the second body portion.

* * * * *